(12) United States Patent
Alonso Diaz et al.

(10) Patent No.: US 9,647,990 B2
(45) Date of Patent: May 9, 2017

(54) METHOD FOR ANONYMOUSLY ASSOCIATING MEASUREMENT DEVICE MEASUREMENTS TO A SOURCE ID

(71) Applicant: Vodafone IP Licensing Limited, Newbury (GB)

(72) Inventors: Patricia Alonso Diaz, Alcobendas (ES); Daniel Almodóvar Herráiz, Alcobendas (ES); Guillermo Esteve Asensio, Alcobendas (ES)

(73) Assignee: VODAFONE IP LICENSING LIMITED, Berkshire (GB)

( * ) Notice: Subject to any disclaimer, the term of this patent is extended or adjusted under 35 U.S.C. 154(b) by 33 days.

(21) Appl. No.: 14/197,939

(22) Filed: Mar. 5, 2014

(65) Prior Publication Data

US 2014/0259133 A1    Sep. 11, 2014

(51) Int. Cl.
| | | |
|---|---|---|
| *H04L 29/06* | (2006.01) | |
| *G06F 19/00* | (2011.01) | |
| *G06F 21/62* | (2013.01) | |
| *A61B 5/00* | (2006.01) | |
| *A61B 5/01* | (2006.01) | |

(Continued)

(52) U.S. Cl.
CPC ........ *H04L 63/0421* (2013.01); *G06F 19/322* (2013.01); *G06F 21/6254* (2013.01); *H04L 63/18* (2013.01); *A61B 5/0022* (2013.01); *A61B 5/01* (2013.01); *A61B 5/021* (2013.01); *A61B 5/11* (2013.01); *A61B 5/14532* (2013.01); *A61B 2562/08* (2013.01); *G06F 19/3418* (2013.01)

(58) Field of Classification Search
CPC ... H04L 63/0421; H04L 63/18; G06F 19/322; G06F 21/6254; G06F 19/3418; A61B 5/0022; G01G 23/3735

USPC ........................................................ 726/6, 22
See application file for complete search history.

(56) References Cited

U.S. PATENT DOCUMENTS 5,626,144 A * 5/1997 Tacklind .............. A61B 5/0002
                                                                600/529
6,219,671 B1 * 4/2001 de Vries ............ G06F 17/30817
(Continued)

OTHER PUBLICATIONS

European Search Report dated Jun. 16, 2014 in corresponding European Application No. 14157470.
ES Search Report for ES P201330310 dated Feb. 27, 12014.

*Primary Examiner* — David Garcia Cervetti
(74) *Attorney, Agent, or Firm* — B. Aaron Schulman, Esq.; Stites & Harbison, PLLC.

(57) ABSTRACT

Proposed invention refers to a method for anonymously associating health monitoring device measurements to a user ID. The invention comprises the steps of: registering in a server a user associated with an ID and a first set of metadata; registering a health monitoring device associated to a second ID and a second set of metadata; then, sending through a first communication channel the ID associated to the user and the first set of metadata to the server by a communication device; taking a measurement of the user by the health monitoring device and sending through a second communication channel said measurement associated to the second ID and the second set of metadata to the server; comparing the metadata stored in the server; and finally associating the first ID with the measurements taken by the health monitoring device corresponding to the second set of metadata, being based the association on the results of the previous comparison.

15 Claims, 2 Drawing Sheets

(51) Int. Cl.
  *A61B 5/021* (2006.01)
  *A61B 5/11* (2006.01)
  *A61B 5/145* (2006.01)

(56) References Cited

U.S. PATENT DOCUMENTS

| | | | | |
|---|---|---|---|---|
| 6,336,900 | B1* | 1/2002 | Alleckson | G06F 19/3412 128/904 |
| 6,602,191 | B2* | 8/2003 | Quy | G06F 19/3406 128/903 |
| 6,974,413 | B2* | 12/2005 | Bardy | A61B 5/0002 600/300 |
| 6,976,958 | B2* | 12/2005 | Quy | G06F 19/321 128/903 |
| RE39,871 | E* | 10/2007 | Skardon | G06F 19/3418 340/517 |
| 7,468,032 | B2* | 12/2008 | Stahmann | A61B 5/0031 600/301 |
| 7,519,430 | B2* | 4/2009 | Von Arx | A61N 1/37223 607/60 |
| 7,647,185 | B2* | 1/2010 | Tarassenko | A61B 5/0245 702/19 |
| 7,689,437 | B1* | 3/2010 | Teller | A61B 5/411 600/300 |
| 7,818,067 | B2* | 10/2010 | Healy | A61N 1/37211 607/60 |
| 7,860,574 | B2* | 12/2010 | Von Arx | A61N 1/37223 607/60 |
| 7,983,745 | B2* | 7/2011 | Hatlestad | A61B 5/0031 600/513 |
| 8,126,729 | B2* | 2/2012 | Dicks | G06F 19/3418 600/300 |
| 8,126,731 | B2* | 2/2012 | Dicks | G06F 19/3418 600/300 |
| 8,126,732 | B2* | 2/2012 | Dicks | G06Q 50/22 600/300 |
| 8,131,754 | B1* | 3/2012 | Lawrence | G06F 17/30864 707/758 |
| 8,631,050 | B1* | 1/2014 | Gayle | G06F 17/30569 707/602 |
| 8,968,195 | B2* | 3/2015 | Tran | A61B 8/06 600/300 |
| 9,047,455 | B2* | 6/2015 | Dietrich | G06F 21/31 |
| 9,526,456 | B2* | 12/2016 | Bardy | A61B 5/7275 |
| 2004/0073093 | A1* | 4/2004 | Hatlestad | A61B 5/1116 600/300 |
| 2004/0078238 | A1* | 4/2004 | Thomas | G06F 19/321 705/3 |
| 2004/0167465 | A1* | 8/2004 | Mihai | A61B 5/0002 604/67 |
| 2004/0167804 | A1* | 8/2004 | Simpson | A61B 5/0002 705/3 |
| 2004/0172222 | A1* | 9/2004 | Simpson | G06F 19/3418 702/189 |
| 2004/0172300 | A1* | 9/2004 | Mihai | A61B 5/0002 705/2 |
| 2004/0172301 | A1* | 9/2004 | Mihai | A61B 5/0002 705/2 |
| 2004/0172302 | A1* | 9/2004 | Martucci | A61B 5/0002 705/2 |
| 2005/0055242 | A1* | 3/2005 | Bello | G06Q 50/22 705/2 |
| 2005/0055244 | A1* | 3/2005 | Mullan | G06Q 50/22 705/2 |
| 2005/0065817 | A1* | 3/2005 | Mihai | A61B 5/0002 705/2 |
| 2005/0119941 | A1* | 6/2005 | James | G06F 19/322 705/2 |
| 2007/0124116 | A1* | 5/2007 | Liu | G01D 21/00 702/189 |
| 2007/0282988 | A1* | 12/2007 | Bornhoevd | G06Q 10/00 709/223 |
| 2007/0283002 | A1* | 12/2007 | Bornhoevd | G06F 9/54 709/224 |
| 2008/0181405 | A1* | 7/2008 | Seppanen | H04L 9/0637 380/270 |
| 2008/0259919 | A1* | 10/2008 | Monga | H04L 43/12 370/389 |
| 2009/0144021 | A1* | 6/2009 | Ketskes | G01G 19/4146 702/173 |
| 2009/0205042 | A1* | 8/2009 | Zhou | G06F 19/3418 726/19 |
| 2010/0001862 | A1* | 1/2010 | Wilson | G07D 7/0093 340/572.1 |
| 2010/0169712 | A1* | 7/2010 | Argue | G06F 11/079 714/25 |
| 2010/0315225 | A1* | 12/2010 | Teague | A61B 5/0024 340/539.12 |
| 2011/0191829 | A1* | 8/2011 | Fischer | H04L 12/22 726/4 |
| 2011/0313774 | A1* | 12/2011 | Ji | G06F 19/322 704/275 |
| 2012/0009676 | A1* | 1/2012 | Mack | C12N 5/0696 435/372 |
| 2012/0030229 | A1* | 2/2012 | Ji | G06F 19/322 707/769 |
| 2012/0086568 | A1* | 4/2012 | Scott | G05B 15/02 340/501 |
| 2012/0109676 | A1* | 5/2012 | Landau | G06Q 50/22 705/2 |
| 2012/0122430 | A1* | 5/2012 | Hutchings | G01G 19/44 455/414.1 |
| 2012/0163520 | A1* | 6/2012 | Liu | G01S 5/0018 375/356 |
| 2012/0197852 | A1* | 8/2012 | Dutta | H04L 67/2804 707/692 |
| 2012/0197856 | A1* | 8/2012 | Banka | H04L 67/2885 707/706 |
| 2013/0024928 | A1* | 1/2013 | Burke | H04L 63/0272 726/12 |
| 2013/0124671 | A1* | 5/2013 | Hunter | G06Q 30/0623 709/217 |
| 2013/0127904 | A1* | 5/2013 | Dove | G06F 3/0488 345/629 |
| 2013/0151666 | A1* | 6/2013 | Hunter | G06Q 30/00 709/219 |
| 2013/0159454 | A1* | 6/2013 | Hunter | H04L 67/125 709/217 |
| 2013/0215042 | A1* | 8/2013 | Messerschmidt | G06F 3/041 345/173 |
| 2013/0317325 | A1* | 11/2013 | Wood | A61B 5/14551 600/310 |
| 2014/0172366 | A1* | 6/2014 | Hannebutte | G06K 9/00496 702/181 |
| 2014/0207489 | A1* | 7/2014 | Wartena | G06F 19/3487 705/3 |
| 2014/0278259 | A1* | 9/2014 | Neeley | G01D 7/08 702/189 |
| 2014/0316805 | A1* | 10/2014 | Nagata | G06F 19/3406 705/2 |
| 2014/0361906 | A1* | 12/2014 | Hughes | H04W 84/18 340/870.01 |
| 2015/0223733 | A1* | 8/2015 | Al-Alusi | A61B 5/0507 600/479 |
| 2015/0248275 | A1* | 9/2015 | Gallo | G01T 7/00 702/189 |

\* cited by examiner

METHOD FOR ANONYMOUSLY ASSOCIATING MEASUREMENT DEVICE MEASUREMENTS TO A SOURCE ID

TECHNICAL FIELD OF THE INVENTION

Present invention has application in the field of security and privacy of data. More particularly, the invention focuses on the protection of data sent and guarantee the privacy of the sources by describing a method for anonymously associating monitoring device measurements to a source ID.

BACKGROUND OF THE INVENTION

Nowadays, unstoppable growing of communication techniques involves several advantages and new ways of transmitting data which were unthinkable not long ago. It is common collecting any kind of data from anywhere just by adding a communication module to any device.

One may think in tracking systems used by the postal service or delivery companies, the big amount of data collected in the cities by means of different sensors placed on the streets or the health devices used for monitoring chronic patients allowing supervision from hospitals.

As the number of communications is increasing and more and more data are travelling through the air, the risk of non-authorized people catching data is also a fact.

Thus, security of data or data protection turns in a main issue in the current context, concerning both people (protective with their own data) and governments (legislating to protect people anonymity to certain extent).

It is known from prior art a bunch of solutions related to send health measurements of patients who use a wide variety of health devices like blood pressures, weight scales or glucometers with capacity to send said measurements remotely to doctors for their supervision from hospitals and assistance centres or patient's homes. Or according to a feasible scenario where a single health device is used by several users in a public space, as a nursing home, it is needed to associate each medical measurement with the person and it is here where the problem about anonymity, and the specific requirements of many cases, arises.

The prior art discloses some inventions regarding this item, for example US201209676 (A1) "Multiuser health monitoring using biometric identification" where it is presented a health monitoring hub, system and method for remotely monitoring a person's health. This patent provides a method to pair the measurement with the identifier of the person either in a local or remote hub. However, this method may be valid when the requirements about privacy and data protection laws are relaxed, but certainly it is insufficient for strict Privacy bills, as most European countries where medical data is considered extremely sensible and thus requiring specific methods of protection.

Also the patents US20120030229A1 and US20110313774A1 describe a method to associate measures to a user using time stamps, but the main problem of these patents is that a solution based on time stamps is only valid for a reduced group of users and the users anonymity cannot be guaranteed.

Another solution proposed in the prior art is US2009205042A "External user interface based measurement association", where the patient "Identifies herself" and there is a step of associate measurements with patients ID (this uses a "remote device" against an "Identification device" that communicates with an "Association device" that after the association, transfers the data to the "measurement server", but all this process implies a single channel of communication or at least, two channels closely related, what may put the anonymity at risk. The binding user-measurement is done locally in the "patient station" despite the session method described. The purpose of this solution is far from fulfilling strict data protection bills but it seems a method for allowing many measurements from a single user that are useful for purposes of a rehabilitation session, as for example physiotherapy exercises for recovering a damaged member.

Same problem with anonymity is repeated in many cities where they have deployed sensor networks, cameras and all kind of measurement devices to monitor for example the traffic of certain streets, the influx of people in certain locations of the city . . . all these data are highly valuable and need to be protected. The classical solution is resorting to complex coding techniques which are not suitable for these cases where actually all these data are useless if they cannot be correctly matched with the associated source. Therefore the focus should be on the matching.

In general, any system working with big amounts of sensitive data associated to sources, resort to complex coding algorithms to send the data, but these solutions are not actually avoiding the risk of a third person catching the data since they often use the same channel to be transmitted.

Even, if the data of the sources are not sent together with the identification of the sources, the links are almost obvious for any one skill in the art and interested in obtaining certain unauthorized data.

Besides the anonymity issue, the protection of data associated to the user prevents for robberies. For example delivery companies often use tracking systems monitoring their goods, as it is also used in containers or trucks. Data related with the content and progressing of a shipment in containers/packets/trucks need to be associated in some way to the source (an identifier for the container/packet/truck for example) but once the data and the identifier are sent to a control system they are exposed to be intercepted by a third party.

Therefore, it is missing in the prior art a method for anonymously associating users to the measurements taken by measurements devices. Measurements and identification travel together or obviously linked in all the solutions commented before or even a matching is done locally, which is highly inappropriate to guarantee the anonymity of the service.

SUMMARY OF THE INVENTION

The present invention serves to solve the aforesaid problems by enabling the association between a source, using a communication device such as a mobile phone, and measurements from a measurement device which can be used by several users providing anonymity and security. The solution proposed is that measurements and identifications travel separately, absolutely uncorrelated. The association takes only place in a server owning all the information of the sources. To this purpose it is presented a method for anonymously associating measurement device measurements to a source ID. The method is characterized by comprising the steps of:

a) registering (1) a source in a server, being assigned a first ID to the registered source associated to a first set of metadata;

b) registering (2) a measurement device in a server, being assigned a second ID to the registered measurement device associated to a second set of metadata;

c) sending (3) through a first communication channel the first ID and the first set of metadata to the server by a communication device associated to the source;

d) taking a measurement of the source by the measurement device and sending (4) through a second communication channel said measurement associated to the second ID and the second set of metadata to the server;

e) comparing in the server metadata the first set of metadata with all the sets of metadata (5) sent to the server by measurement devices registered in the server;

f) associating (7) in the server the first ID with the measurements taken by the measurement device corresponding to the second set of metadata, being based the association on the results of the comparison of previous step.

The comparing can be tuned by setting a threshold (14) for the values of each of the metadata to be compared. Thus, different ranges of elements may be obtained and the method fits properly to the different cases.

The compared metadata may be obtained by a direct match (6) from both the first and the second set of metadata, although additionally, the method may also comprise inference rules (10) relating (11, 12, 13) at least two specific metadata.

In one embodiments of the invention, the metadata taken to be compared are combined in groups of at least two elements. Logical conditions are associated to said elements based in the similarities.

Optionally, the invention may refine the comparison by increasing iteratively (9) the number of metadata elements taken to be compared. The association that the method proposes may be finally added to an historical file associated to the source.

Proposed invention may comprise that the communication device associated to the source and the measurement device are communicated before sending anything to the server. The communication device, according to one embodiment of the invention is a mobile phone and, according to one particular embodiment, the association proposed by the invention is sent to the mobile phone prompting to be accepted by a user supervising the operation.

The metadata considered in one embodiment of the invention are selected from the following list: time, date, serial number, frequency of use, environmental light, environmental temperature, pressure and movements over a screen, location, data from networks at range or any other data gathered by one or both the measurement device and the communication device associated to the source. Also, certain logic may be comprised to compare non-numerical metadata.

According to one embodiment of the invention, the measurement devices may comprise health monitoring devices. For example blood pressures, weight scales or glucometers.

Some embodiments of the invention refers to measurement devices comprising sensors for tracking deliveries, monitoring a fleet of vehicles or sensors for measuring affluence/traffic of certain locations.

A second aspect of the invention refers to a system for anonymously associating measurement device measurements to a source ID, being the system characterized by comprising:

a communication device configured for sending a first ID and a first set of metadata to a server;

a measurement device configured for taking a measurement of a source and sending said measurement associated to a second ID and a second set of metadata to the server;

a server configured for receiving messages from the communication device and the measurement device, comparing metadata comprised in the messages and associating the first ID to the measurements taken by the measurement device according to the result of the comparison.

Another aspect of the invention refers to a server for anonymously associating a measurement device measurements to a source ID, being the server characterized by receiving messages from a communication device and a measurement device, comparing the metadata comprised in the messages and associating the source ID to the measurements taken by the measurement device according to the result of the comparison and a certain logic.

In one embodiment of the invention it is presented a method for anonymously associating health monitoring device measurements to a user ID. The method is characterized by comprising the steps of:

a) registering (1) a user in a server, being assigned a first ID to the registered user associated to a first set of metadata;

b) registering (2) a health monitoring device in a server, being assigned a second ID to the registered measurement device associated to a second set of metadata;

c) sending (3) through a first communication channel the first ID and the first set of metadata to the server by a communication device used by the user;

d) taking a measurement of the user by the measurement device and sending (4) through a second communication channel said measurement associated to the second ID and the second set of metadata to the server;

e) comparing in the server metadata the first set of metadata with all the sets of metadata (5) sent to the server by health monitoring devices registered in the server;

f) associating (7) in the server the first ID with the measurements taken by the health monitoring devices corresponding to the second set of metadata, being based the association on the results of the comparison of previous step.

A last aspect of the invention refers to a computer program product comprising computer program code adapted to perform the method of the invention when said program code is executed on a computer, a digital signal processor, a field-programmable gate array, an application-specific integrated circuit, a micro-processor, a micro-controller, or any other form of programmable hardware.

DESCRIPTION OF THE DRAWINGS

To complete the description that is being made and with the object of assisting in a better understanding of the characteristics of the invention, in accordance with a preferred example of practical embodiment thereof, accompanying said description as an integral part thereof, is a set of drawings wherein, by way of illustration and not restrictively, the following has been represented.

DETAILED DESCRIPTION OF THE INVENTION

Proposed invention enables the association between a source using a communication device and a measurement acquired by measurement devices used by several sources providing anonymity.

Figure 1:
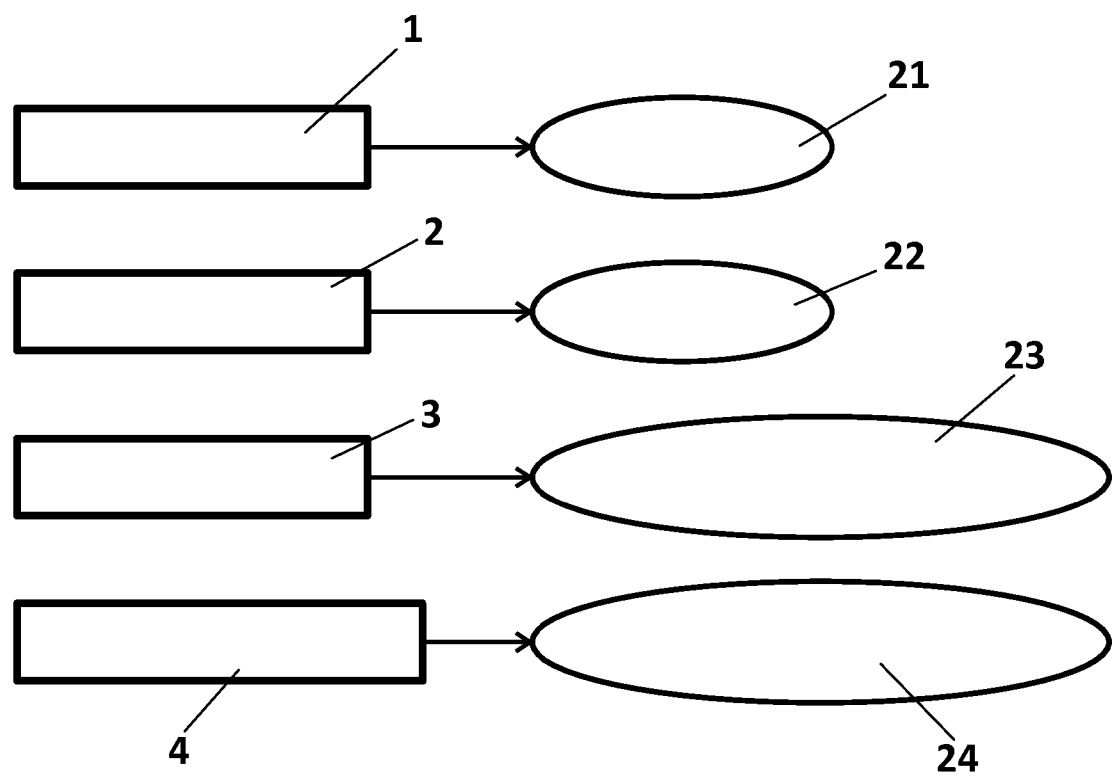
FIG. 1 represents the communications received by the server according to one embodiment of the proposed invention.
Figure 2:
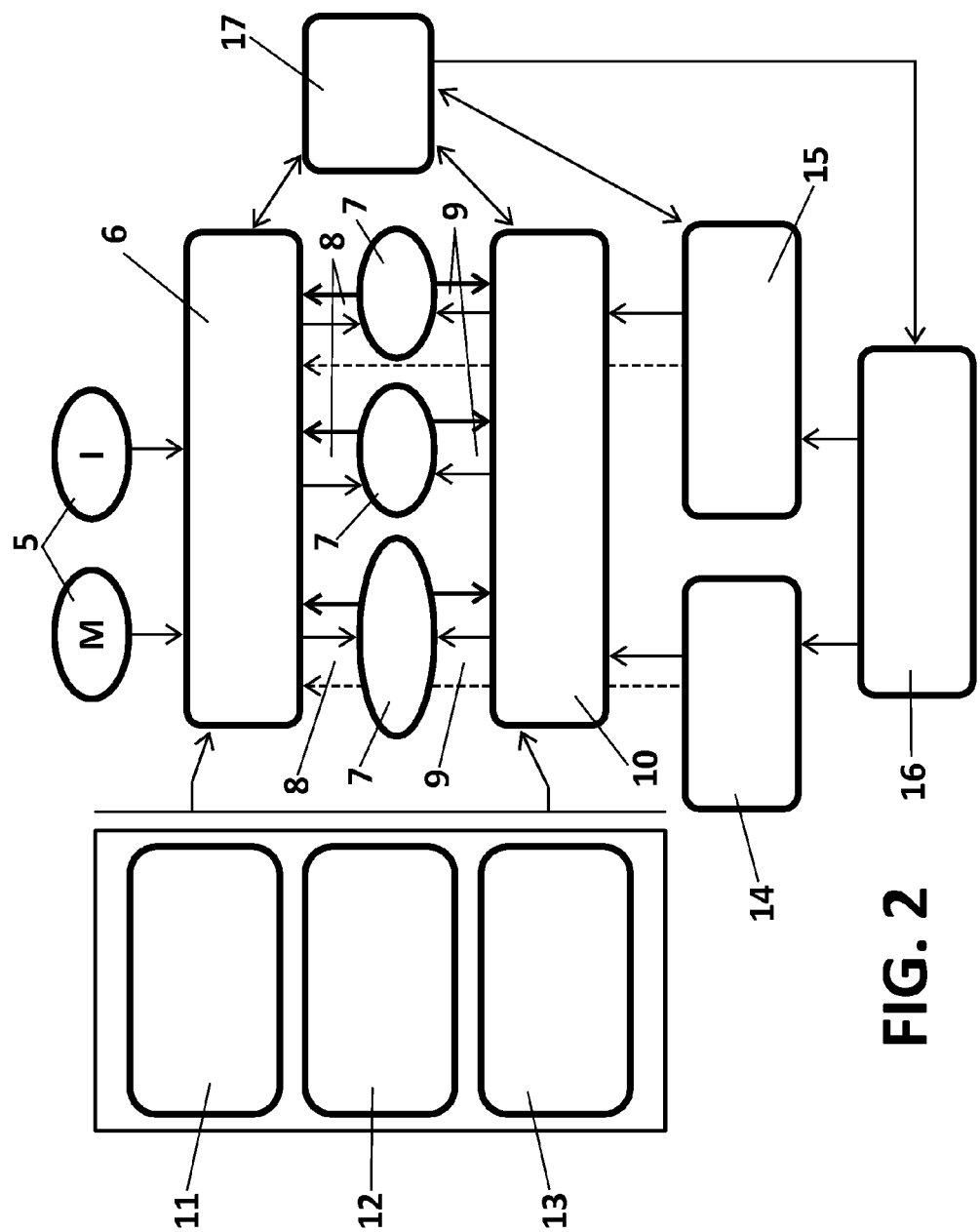
FIG. 2 represents, according to one embodiment of the invention, the process followed in the server to associate source identification with measurements taken by a measurement device.

The data from the measurement device, as a health measurement device, a localization measurement device placed in a truck or a movement sensor in a corner of street are delivered using one communications channel and the data to relate that to a specific source (for example a specific source may be a patient for a health monitoring system, a truck for a tracking system or a localization for traffic/flux system) are sent by the communication device using a different channel. Thus, measurements and identification data are sent independently and totally uncorrelated. The communication channels used by the communication device may vary from one embodiment to another. Example of communication channels used to this end are Short Messages (SMS), data-over-voice connections as FAX or different protocols over data connections (Mail or STMP, Instant Messaging or XMPP, http request, etc . . . ), all of them over several wireless bearers, as WiFi, 3G, LTE, etc. FIG. 1 clearly represents this process according to a particular embodiment of the invention, where after the initial registration of sources (1) and devices (2)—which can happen in any order—and they are assigned with a source ID (21) and a device ID (22) respectively, both elements start delivering messages to the server (3), (4). Those messages $i_i$ (23) and $m_j$ (24) consists in several fields (or vectors) including at least the ID of the source or the device respectively and some metadata elements $d_i$, $d_j$. Those messages belong to either I or M, being I and M the sets of data associated to the sources and the devices respectively. In the case of the set M, the $m_j$ vectors also comprise the measurements taken FIG. 2 describes, according to one particular embodiment, the process followed after the messages of FIG. 1 are sent to the server. The data sets M and I (5) are compared (6) using a direct matching algorithm based on a set of thresholds defining what is considered as "very similar" (14) between two comparable metadata. The metadata to be compared are defined by logic relations (built for example using truth tables) between elements of the metadata of the Source Message, named $d_i$ and the metadata of the Device Measurement, named $d_j$ (11) or between elements of one of the data sets (12), (13). This comparison starts being one-on-one but it evolves to be the combination of many against many.

After this step (6), they are generated three sets (7): one set of pairs of matching Source Messages and Device Measurements $i_i$, $m_j$ and a reduced two sets of remaining elements $M_k'$ and $I_k'$ to be matched. These three data sets are injected (8) either to the same process (6) or passed to (9) the complementary process of inference described before (10) which generates a new set k of the three data sets (7). The subsequent iterations of either one process or the other keep reducing the number of elements in $M_k'$ and $I_k'$ by matching elements or marking them as mistakes.

The overall process is controlled by a Control process (17) receiving information from the two mentioned process (6) and (10) and from a set of adjustable stop conditions (15) to decide that the state of process (6) or (10) is reasonable good and rules to mark elements as mistakes or errors (15). These stop conditions and rules can be adjusted by the control process to define the next iteration or if there will be another iteration at all.

Additionally, the thresholds which define "very similar" (14) may be adjusted by a process (16) controlled by the control process (16), affecting the way that the process (6) and (10) run each iteration.

The following elements are included:

A communication device (e.g. a mobile phone) which sends the information of the source identifier together with some metadata. The source identifier (ID) is any data that leads to a source previously registered in the service. This may be any number or text string but also, any biometric pattern, as voice pattern, fingerprint, face/iris recognition or the like. Examples of metadata used in different embodiments are location, time, a device identifier (as serial number), type and frequency of use of the device and of the applications in the device (historical and current), environmental light, environmental temperature, movement vectors and patterns (as a specific sign drawn with the communication device), pressure (over screen or buttons), images, contacts, data from networks in use or at range (WiFi, Bluetooth, 3G cell ID, etc), gateways used (Known as APNs in mobile networks), or any data gathered with the communication device.

A measurement device—as a health monitoring device such as a blood pressure, a weight scale, a glucometer, or any other device used for health monitoring; a localization measurement device placed in a truck such as a GPS or movement sensor in a corner of street—which takes the measurement of the sources. This device transmits messages by any of the means mentioned before as "communication channels". It is also considered the possibility to connect said device, according to another embodiment, to the communication device of the source to use their capabilities and transmit a separate and unrelated message. In this later case the anonymity is more relaxed than the general procedure described due to a same communication device is used.

A server configured to receive the two pieces of information (the source identification data from the communication device and the value of the measurement from the measurement device) and then associate the source identity with the measurement taken.

According to one embodiment of the present invention, sources of the service and devices associated to the service are registered in a server in order to use the proposed method, so they have a unique ID. Alternatively, in another embodiment of the invention, the unique ID is assigned on first use, as a self-provisioning system.

During the registration process, the source associate his ID with some data used as metadata as an identifier of the communication device ID. Then, during each measurement, the source sends information to the server to identify himself, for example said communication device ID together with some metadata of the measurement. At approximately the same time, the measurement device sends to the server the value of the measurement, some metadata of the measurement (as the time, the location . . . ) and the measurement device ID (for example the MAC address of the device). Then the server collects this information and compares it with its previously uploaded metadata of each source to associate the value from the measurement device with the corresponding ID source.

The metadata configured in the server for each source ID additionally may contain the historic values of measurements. A big range of metadata can be used. As examples of metadata of the measurement device, it can be chosen any from the following list: time; device identifier (as serial number); type and frequency of use of the device and of the features in the device (historical and current); environmental light (if available); environmental temperature(if available); pressure and movement vectors and patterns (depending of the device); data from networks in use or at range(WiFi, Bluetooth, 3G cell ID, etc); gateways used (Known as APNs in mobile networks), or any data gathered with the device; in this last group, there might be any data provided by the communication device as the mere proximity of the communication device, the location, pressure (over screen or buttons); images; contacts; etc. excluding Source ID, of course, to guarantee anonymity.

The comparing is done in the server, which has all the information from all the sources and makes impossible to match the information in any other place. Realistic scenarios with millions of sources demonstrate that time-based metadata is only applicable when a few sources are using a service, in a typical environment of millions of concurrent messages; time is of little use as you can have thousands of simultaneous measurements with timestamps of un-synchronized clocks arriving with different travel times.

Focusing on the comparing step, and according to the previous embodiment, it is considered that the set of measurements M has a number of elements m equal in the long term to the set of elements of identification i of the set I. Typically, m and i are vectors containing several metadata values in addition to the measured values and the identification of the device and measurements. A binary association between both sets is made minimizing errors. The matching is iterative and over each set of metadata, as the time stamp or the historic values of the user used as an example because they are quite intuitive, but it is not sequential but inclusive so after considering one metadata that one and another are considered. Other sets of information less used are the environmental values (wireless networks present, pressure and temperature . . . ) measured at the point of the measurement by both elements at approximately the same time.

Some sources are very predictable due to their metadata (for example stable weight/blood pressure and regular measurements from the same place at the same hour, or a recurrent path covered by a truck the same day of the week) but some of them are really unpredictable making the association impossible if it is faced individually. However, isolating said sources by discarding any other association, it is finally made a match of uncorrelated data. According to one embodiment of the invention, said matching does not need to be immediate (real time) but different sets of M and I are used expanding and contracting a timespan and/or area and varying a threshold for each metadata (for instance, to match all the measurements in a certain range of weight against all the IDs using all the metadata available, the threshold for the weight is increased each time the method is run). The comparison of enough unbalanced subsets can converge to make the binary association of the balanced sets.

Additionally, the ranges to compare are bigger or smaller (for example of time periods) so the unmatched pairs can converge to a single one considering one metadata, reducing the number of options to match considering another metadata until reaching a reasonable result.

Some other pairs of messages are easily to match even without prior knowledge of the source habits or data, as two messages that has the same set of WiFi networks detected among their metadata in a short time range. The non-numerical metadata needs certain logic to be compared. These easy matches reduce the options for the impossible matches and given enough metadata and ranges on each, it is possible to converge in most cases.

A specific example of implementation is disclosed below related to a health monitoring system:

i) The user (source) registers himself in the health monitoring service to upload data from measurement devices. This generates a user identifier (userID) D) unique to him in the service. The service provided to the user consists in the safe reception, storage and management of measurements related to him taken by any of the devices that works with the service.

ii) This userID is used in communication devices to indicate to the server that the user has interacted with a device covered by the service and some measurements have been taken. The communication device is, in this example, a smartphone running an application where the user logs-in with the ID and has a "red button" to just say "done".

iii) The measurement devices can be owned by the user or publicly available, for example a weight scale. This device is connected to internet by any mean (wired or wireless) and has some capabilities to automate the process described in this example. The measurement devices are also registered in the service and have a unique measurement device identifier too; this registration means that they are allowed to deliver measurements to the server.

iv) Once the previous steps are done—continuing with this example—the user wants to measure his weight. So he uses one of the weight scales registered in the service and steps on. This makes the weight scale to send a message to the server with the measurement and all the possible metadata surrounding the measurement.

v) Before, or after or while on the weight scale, the user presses the "red button" on the smartphone. This makes the device to send a message to the server with the userID and all the possible metadata. The list of metadata can be the same of the measurement device, but it is not necessary, as the smartphone and the weight scale can have different capabilities to capture metadata. Both messages are totally independent and unrelated so in order to associate both of them it is needed some logic that is only run in the server.

vi) The metadata, as it was commented before can be many things and can be determined by several methods. For example, about the location, the smartphone can measure it using its GPS and the weight scale can have it assigned at the server. The list of possible metadata is already disclosed, but some of them should be avoided in one of the sets of metadata to guarantee that the correlation between messages (from smartphone and from weight scale) does not compromise the anonymity of the measurement.

vii) Then, at the server, there are two sets of messages, one set M of measurements coming from measurement devices and other of set I of identifications coming from communication devices where the users pressed the red button. The anonymity is given not only by the unrelated delivery but also by the large numbers of elements in both sets.

viii) The algorithm in the server compares and matches as many pairs as possible minimizing errors.

Only a server with all the messages from both sets M and I can run the following process with the same success ratio, so the level of protection is really high.

Different strategies give different success ratios and combining them leads to the optimal solution. The strategies comprised are:
A) Isolating elements from each set, so they must pair due to a direct match in a specific metadata. For example if elements from each set shows the same list of wireless networks at reach with "very similar" power levels they are paired ignoring timestamps of both messages.
B) Pairing elements based in similarities in two or more elements of the metadata (for example the combination of location and time). For computer optimization reasons, this is launched iteratively and incrementally.
C) Using inference rules derived from the logic, relating different elements of the metadata to compare elements. For instance, if the metadata of a user identification gives a certain temperature it should match with a set of known measurement devices' locations (indoors, for instance) and times depending on the season.
D) Modifying the ranges of values for each metadata element increasing and decreasing the definition of "very similar" values. For example, if there are several elements already matched (by any strategy) it can be expanded the range to include just an unmatched element of each set so they can be matched despite there were not any direct connection between them. There are some logic rules in the range definition as some metadata elements are not numerical, for example, the list of wireless networks within range requires a weighting function to transform it in computer-comparable values. This also works when the data range adaptation results in one element of one set against several of the other and the server then launch a sub-process to choose the best match among them. This also works when the definition of "very similar" is adjusted for two or more metadata elements at the same time. In fact the more metadata elements involved the better the comparison but this has to be launched iteratively (increasing elements used) for optimization of the computation resources.
E) Marking impossible matches (as the opposite of "very similar"), so the elements of both sets are reduced to a direct match. Also this can give one element in one set against several in the other and launch a sub-process to find the least-worst match.

In one embodiment of the invention is considered the handling of erroneous messages, which affects the algorithm to compare messages. Examples of errors are the case of users delivering messages of "measurement being taken" without actually taking any measurement and the measurement device taking measurements of individuals who are not registered in the service. In this case it is defined a procedure to discard either measurements or source data messages where a user has to review the historic values later in the server by any telematic mean as a web interface for example, in order to accept or reject said measurement, or directly an additional step consisting on, once the matching has led to make an association source-measurement, sending to a user an acknowledge message from the server prompting said association to be accepted or correcting the association in case of error. For example the server would deliver the value measures (as weight) to the communication device so it is displayed and the user can approve or refuse the value as own. It has to be noted that a user itself may also be the source. Other example is that the server delivers an identifier to the measurement device so the user can know if he has been correctly identified and accept or refuse the association. This increases the information gathered by the server and improves the percentage of correct associations and also, since new information is given to the system, other erroneous associations can be solved without the intervention of other users affected.

Another embodiment of the invention avoids that the measurement device and/or the communication device delivers erroneously its message in the case that there are metadata not attainable or absent, as for instance the presence of the other element (both elements broadcast their identifier as part of the metadata and the other can recognizes it). Although this does not mean that the presence of the other device must be included in the metadata.

The measurement device can be employed by several sources, for example a weight scale for trucks. The communication device can also be used by several sources assuming that there is a mean to select the current user in it, so the correct user ID is selected.

At the end, the association of source identification and measurements taken by health monitoring devices is used to remotely determine the most appropriate medical indications or treatments to the user. As it has been demonstrated, the anonymity is total, so the client can be confident about the privacy of his data and health measurements, which is a delicate issue which has not been solved in the prior art.

Another specific example of implementation is disclosed below related to a logistic monitoring system:
The user registers a delivery (source) in the service to upload data from the communication device of this delivery. The communication device of the delivery might be a tracker, keyless mobile phone, etc. This generates a delivery identifier (deliveryID) unique to it in the service. The service provided to the user consists in the safe and anonymous reception, storage and management of measurements related to the delivery taken by any of the devices that works with the service.
This delivery ID is used in communication devices to indicate to the server that the user has interacted with a device covered by the service and some measurements have been taken. A communication device suitable for this example is a keyless mobile phone connected to several sensors running an application which sends a set of metadata at given time intervals, when an event happens or a mix of both. Examples of events are crossing a gate frame of a warehouse, receiving a command to send the metadata, or surpassing a threshold on any of the sensors connected to the communication device.
The measurement devices and elements can be owned by the user or publicly available, for example a warehouse thermometer or weather information. These devices and elements are connected to internet by any mean (wired or wireless) and have some capabilities to automate the process described in this example. The measurement devices are also registered in the service and they have a unique measurement device identifier too; this registration means that they are allowed to deliver measurements to the server.
Once the previous steps are done—continuing with this example—the user wants to control that the delivery is below a given temperature during its journey. So he sets the communication device to send the information whenever it detects a change of location by crossing gate frames or just at given intervals. Similarly, sets the thermometer to send a message to the server with the measurement and all the possible metadata surrounding the measurement whenever a new good enters or exits the warehouse or at a given intervals.

The list of metadata can be the same for the communication device and for the measurement device, but it is not necessary, as the communication device and the thermometer can have different capabilities to capture metadata. Both flows of messages are totally independent and unrelated so in order to associate both of them it is needed some logic that is only run in the server. Location information may be available or not.

Metadata can be many things and can be determined by several methods. For example, about the location, the communication device of the delivery can measure it using its GPS and the thermometer can have it assigned at the server. The list of possible metadata is already disclosed, but some of them should be avoided in one of the sets of metadata to guarantee that the correlation between flows of messages (from communication device and from thermometer) does not compromise the anonymity of the measurement.

Then, at the server, there are two sets of messages, one set M of measurements coming from measurement devices and other of set I of identifications coming from communication devices of the deliveries. The anonymity is given not only by the unrelated delivery but also by the large numbers of elements in both sets.

The algorithm in the server compares and matches as many pairs of data flows as possible minimizing errors. Only a server with all the messages flows from both sets M and I can run the following process with the same success ratio, so the level of protection is really high. Different strategies give different success ratios and combining them leads to the optimal solution. The strategies comprised are the same than in the previous example.

At the end, the association of delivery identification and measurements taken by measurement devices is used to remotely determine the status of the load and assure its quality. This allows all loads (even medical drugs) to be treated anonymously impeding the identification of the parcel, decreasing the possibility to be stolen, but keeping the good controlled, which is a delicate issue. Similarly, this case can be applied to luggage handling or livestock transportation, as pets and exotic specimens.

Another example of implementation mixing the above examples can be applied to a set of employees using a fleet of vehicles. The example here refers to a user who just uses an application running at a smartphone sending a message to the server stating "I'm starting/stopping to use any of the vehicles of the company" (with the associate metadata) and measurement devices at the vehicle sending regular updates. The matching between both can be done at the server guaranteeing the anonymity between both. This case makes little sense in a standard organization but it is of application for security companies, police and military fleets.

Another specific example of implementation is disclosed below related to obfuscation of a monitoring system:

The user has a monitoring system which comprises a network of measurement devices broadcasting information in a not fully secure manner and wants to impede third parties to use that data. In this example, the monitoring system may comprise affluence meters or traffic load meters as measurement devices. These devices are registered in the service, which generates a device identifier (monitor ID) which is unique in the service. The service provided to the user would consist in a safe and anonymous reception, storage and management of measurements related to the measurement devices.

In this example, the measurement device (source) attains this effect because they do send two separate and independent data flows using the same or different means (wireless or wired). In one of them there are not any monitor ID or similar reference and just upload data to the server; the other data flow uploads their identifier together with some metadata. It is assumed that regular or constant data flows are non synchronized (this is, they have different number of messages per minute at regular or random time intervals)

Then, at the server, there are two flows of sets of messages, one set M of measurements coming from monitoring devices and other of set I of identifications coming from the monitor ID data flow. The anonymity is given not only by the unrelated delivery but also by the large numbers of elements in both sets.

The algorithm in the server compares and matches as many pairs as possible minimizing errors.

Only a server with all the messages from both sets M and I can run the following process with the same success ratio, so the level of protection is really high. Different strategies give different success ratios and combining them leads to the optimal solution. The strategies comprised are the same than in the previous examples.

The invention claimed is:

1. Method for anonymously associating measurement device measurements to a source, the method comprising:
   registering the source in a server, the source being assigned a first ID;
   registering a measurement device in the server, the measurement device being assigned a second ID;
   in response to a measurement of the source being taken by the measurement device, sending, from a communication device associated with the source to the server through a first communication channel, the first ID and a first set of metadata that includes at least one parameter that is not a time parameter;
   upon the measurement of the source being taken by the measurement device, sending, from the measurement device to the server through a second communication channel, the measurement, the second ID, and a second set of metadata that includes at least one parameter that is not a time parameter;
   performing a comparison, in the server, of the first set of metadata with each of a plurality of sets of metadata correspondingly sent to the server by a plurality of measurement devices registered in the server;
   associating, in the server, the first ID with the measurement corresponding to the second set of metadata based on results of the comparison.

2. Method according to claim 1 wherein the comparison comprises setting a threshold for values of each parameter of the sets of metadata being compared.

3. Method according to claim 1 wherein the result of the comparison includes respective values of one specific metadata parameter of the first and second sets of metadata being identified as a direct match.

4. Method according to claim 1 wherein the comparison comprises inference rules relating at least two metadata parameters.

5. Method according to claim 1 wherein metadata parameters used for the comparison are combined in groups of at least two parameters.

6. Method according to claim 5 further comprising refining the comparison by increasing iteratively a number of metadata parameters used for the comparison.

7. Method according to claim 1 wherein the communication device associated with the source and the measurement device are each configured to broadcast a corresponding identifier as part of the first and second sets of metadata respectively and to wait until recognizing the identifier broadcast by the other of the communication device and the measurement device before sending any data to the server.

8. Method according to claim 1 wherein parameters of the sets of metadata are selected from the following list: time, date, serial number, frequency of use, environmental light, environmental temperature, pressure and movements over a screen, location, data from networks at range, and any other data gathered by both the measurement device and the communication device associated with the source.

9. Method according to claim 1 wherein the measurement devices registered in the server comprise health monitoring devices.

10. Method according to claim 1 wherein the measurement devices registered in the server comprise sensors for tracking deliveries, monitoring a fleet of vehicles, or measuring affluence/traffic of certain locations.

11. Method according to claim 1 wherein the communication device associated with the source is a portable computing device with communication capabilities as a mobile phone or a tablet.

12. Method according to claim 1 wherein the comparison involves comparing non-numerical metadata parameters.

13. A non-transitory computer-readable storage medium having computer program code embodied thereon, the program code being executable by a processor to implement the method of claim 1.

14. System for anonymously associating measurement device measurements to a source ID, the system comprising:
- a communication device configured to, in response to a measurement of a source being taken, send a first ID and a first set of metadata comprising a plurality of parameters to a server through a first communication channel;
- a measurement device configured to take the measurement of the source and send the measurement, a second ID, and a second set of metadata comprising a plurality of parameters to the server through a second communication channel;
- a server configured to receive messages from the communication device and the measurement device, perform a comparison of corresponding parameters of the sets of metadata included in the messages, and associate the first ID with the measurement taken by the measurement device according to results of the comparison.

15. Server for anonymously associating measurement device measurements to a source ID, the server comprising:
- an interface that receives messages sent from a communication device through a first communication channel and from a measurement device through a second communication channel; and
- a matching component that compares respective values of a plurality of metadata parameters included in each of the messages and associates the source ID with measurements taken by the measurement device according to results of comparing the respective values of the metadata parameters included in the messages.

* * * * *